(12) United States Patent
Bougaret et al.

(10) Patent No.: US 6,890,558 B2
(45) Date of Patent: May 10, 2005

(54) ORAL PHARMACEUTICAL COMPOSITION FOR SOFT CAPSULES CONTAINING VINORELBINE AND METHOD OF TREATMENT

(75) Inventors: Joel Bougaret, Francarville (FR); Elie Leverd, Castres (FR); Marie-Madeleine Bohn, Auenheim (FR); Norbert Heintz, Forstfeld (FR)

(73) Assignee: R.P. Scherer Technologies, Inc., Las Vegas, NV (US)

( * ) Notice: Subject to any disclaimer, the term of this patent is extended or adjusted under 35 U.S.C. 154(b) by 27 days.

(21) Appl. No.: 10/161,454

(22) Filed: May 31, 2002

(65) Prior Publication Data

US 2003/0224042 A1 Dec. 4, 2003

(51) Int. Cl.[7] .............................. A61K 9/48; A61K 9/64
(52) U.S. Cl. ........................................ 424/456; 424/451
(58) Field of Search ................................ 424/440, 455, 424/456, 451; 514/348, 365

(56) References Cited

U.S. PATENT DOCUMENTS

| | | | | |
|---|---|---|---|---|
| 4,623,629 | A | | 11/1986 | Kerschensteiner .......... 436/518 |
| 5,114,919 | A | * | 5/1992 | Baldwin et al. .............. 514/11 |
| 5,292,512 | A | | 3/1994 | Schaefer et al. ............ 424/401 |
| 5,620,985 | A | | 4/1997 | Jacquesy et al. ............ 514/283 |
| 5,645,856 | A | * | 7/1997 | Lacy et al. .................. 424/455 |
| 6,127,377 | A | | 10/2000 | Duflos et al. ................ 514/283 |
| 6,197,760 | B1 | | 3/2001 | Struck ......................... 514/126 |
| 6,235,761 | B1 | * | 5/2001 | Hartman et al. ............ 514/348 |
| 6,262,093 | B1 | * | 7/2001 | Camden ...................... 514/365 |
| 6,310,039 | B1 | | 10/2001 | Kratz ............................ 514/8 |

FOREIGN PATENT DOCUMENTS

| | | |
|---|---|---|
| EP | 375520 B1 | 4/1993 |
| EP | 010 458 | 4/1998 |

OTHER PUBLICATIONS

Zhou et al, Relative Bioavailability of Two Oral Formulations of Navelbine in Cancer Patients, 1994, Biopharmaceutical & Drug Disposition, vol. 12, 577–586.*

Zhou et al, Relative Bioavailability of Two Oral Formulations of Navelbine in Cancer Patients, 1994, Biopharmaceutics & Drug Disposition, vol. 12, 577–586.*

Rowinsky et al., "Pharmacokinetic, Bioavailability, and Feasibility Study of Oral Vinorelbine in Patients with Solid Tumors," *J. Clin. Oncol.*, vol. 12 (9) (Sep. 1994), pp. 1754–1763.

Zhou et al., "Relative Bioavailability of Two Oral Formulations of Navelbine in Cancer Patients." *Biopharmaceutics & Drug Disposition*, vol. 15 (1994). pp. 577–586; and.

Jassem et al.. "A Multicenter Randomized Phase II Study of Oral vs. Intravenous Vinorelbine in Advanced Non–small-cell Lung Cancer Patients." *Annals of Oncology*, vol. 12 (2001) p. 1375–1381.

* cited by examiner

*Primary Examiner*—Thurman K. Page
*Assistant Examiner*—Micah-Paul Young
(74) *Attorney, Agent, or Firm*—Andrew G. Rozycki; Donald O. Nickey

(57) ABSTRACT

The invention described herein relates to a pharmaceutical composition containing vinorelbine as an active ingredient which is suitable for encapsulation in soft capsules. The liquid oral pharmaceutical composition suitable for a liquid fill composition for a soft capsule dosage form comprises: vinorelbine or a pharmaceutically acceptable salt thereof; ethanol; water; glycerol; and polyethylene glycol. In a preferred embodiment, the tartrate salt form of vinorelbine is used in the composition. The invention also provides for a method of treating cancer comprising orally administering, to a patient in need of treatment thereof, a soft capsule comprising the pharmaceutical composition of the invention.

12 Claims, No Drawings

ORAL PHARMACEUTICAL COMPOSITION FOR SOFT CAPSULES CONTAINING VINORELBINE AND METHOD OF TREATMENT

FIELD OF THE INVENTION

The invention relates to the field of orally administrable pharmaceutical compositions for treating cancer. In particular, the invention pertains to oral dosage forms containing the vinca alkaloid vinorelbine as the pharmaceutically active ingredient.

BACKGROUND OF THE INVENTION

Vinorelbine or 3',4'-didehydro-4'-deoxy-C'-norvincaleucoblastine is a vinca alkaloid derivative compound which exhibits cytostatic effects by inhibiting tubulin polymerization. Vinorelbine inhibits mitosis at the G2+M phase. Vinorelbine and its pharmaceutical salt forms, including the tartrate salt form, are known for both as anti-neoplastic agents and anti-mitotic agents, and have been used in the treatment of non-small cell lung cancer and metastatic breast cancer.

Vinorelbine has been widely administered to cancer patients as part of chemotherapy by parenteral route through intravenous infusion or injection. Although the drug can be administered by a variety of routes, the intravenous route is one of the most commonly used administration forms of vinorelbine because it has been associated with increased bioavailability. Vinorelbine tartrate is currently manufactured in Plantes et Industrie, Gaillac, France.

Oral dosage forms, including soft capsule dosage forms, containing vinorelbine have been investigated for an oral administration route of the drug. The potential use of soft capsule dosage forms to deliver liquid forms of vinorelbine for the treatment of cancers has been investigated in Rowinsky et al., "Pharmacokinetic, Bioavailability, and Feasibility Study of Oral Vinorelbine in Patients with Solid Tumors," *J. Clin. Oncol.*, Vol. 12 (9) (September 1994), pp. 1754–63; Zhou et al., "Relative Bioavailability of Two Oral Formulations of Navelbine in Cancer Patients," *Biopharmaceutics & Drug Disposition*, Vol. 15 (1994), pp. 577–86; and Jassem et al., "A Multicenter Randomized Phase II Study of Oral vs. Intravenous Vinorelbine in Advanced Non-small-cell Lung Cancer Patients," *Annals of Oncology*, Vol. 12 (2001) p. 1375–81.

Nevertheless, development of liquid fill compositions suitable for soft capsule containment has proven difficult. In capsule fill compositions which can be used in conjunction with soft capsules, the active ingredient needs to be in the solubilized state in a solvent mixture. Furthermore, the fill composition as a whole must be chemically compatible with the capsule material and avoid degradation of the material once it has been encapsulated, as well as be inert or reduce adverse chemical interaction with the active ingredient. In the end to be useful, the biological activity of the active ingredient must not be significantly compromised. Accordingly, developmental challenges can arise in balancing all of these characteristics while accounting for the chemical nature of the active ingredient.

There is a need in the pharmaceutical field for orally administrable dosage forms containing vinorelbine as the active ingredient. Moreover, there is a need for capsule fill formulations containing vinorelbine which have improved solubility and stability characteristics and which have effective post-ingestion bioavailability.

SUMMARY OF THE INVENTION

The invention is directed to a pharmaceutical composition containing vinorelbine as an active ingredient which is suitable for encapsulation in soft capsules, and method of treating cancers by oral administration thereof. Accordingly, the invention provides a liquid fill composition for a soft capsule dosage form, said composition comprising:

a) vinorelbine or a pharmaceutically acceptable salt thereof;
b) ethanol;
c) water;
d) glycerol; and
e) polyethylene glycol.

In a preferred embodiment, the tartrate salt form of vinorelbine is used in the composition. In a still more preferred embodiment, the soft capsule composition for encapsulating the fill comprises a mixture of porcine and bovine gelatin.

The invention also provides for a method of treating cancer comprising orally administering, to a patient in need of treatment thereof, a pharmaceutical composition comprising:

a) a pharmaceutically effective amount of vinorelbine or a pharmaceutically acceptable salt thereof;
b) ethanol;
c) water;
d) glycerol; and
e) polyethylene glycol;
wherein said composition is encapsulated within a soft capsule.

DETAILED DESCRIPTION OF THE INVENTION

The term "pharmaceutically acceptable salt" within the context of vinorelbine is meant to indicate that the active ingredient vinorelbine is present in the pharmaceutical composition in its salt form suitable for oral administration. A variety of salt forms known in the art to be useful for compounds such as vinorelbine and other vinca alkaloid derivatives can be used.

The term "pharmaceutically effective amount" within the context of vinorelbine is meant to indicate that the dosage of vinorelbine as the active ingredient is present between the minimum amount which provides the desired pharmaceutical effect but below the amount determined to be toxic to the patient as a whole beyond patient tolerance levels for the intended treatment, while accommodating variability's in patient response. Pharmaceutical effectiveness for vinorelbine can be determined thusly based on exhibited anti-neoplastic and anti-mitotic activities of the drug in vivo.

The invention involves an improved orally administrable pharmaceutical composition comprising vinorelbine suitable for encapsulation within a soft capsule dosage form. It has been discovered that a liquid fill composition containing vinorelbine as an active ingredient can be formulated to provide enhanced solubility and bioavailability for oral administration, while at the same time balance the chemical properties of the various ingredients in a manner suitable for encapsulation within a soft capsule material.

Vinorelbine and its salt forms for preparation of the fill composition of the invention can be prepared by organic synthesis from natural starting materials, or obtained directly from commercial sources.

The amount of vinorelbine, namely the pharmaceutically effective amount of vinorelbine or a pharmaceutically acceptable salt thereof, that can be used in the pharmaceutical composition of the invention can vary provided the amount and concentration of the active ingredient can be solubilized within a fill composition permitting an overall dosage form volume suitable for oral ingestion. The pharmaceutical composition of the invention can comprise base amounts of vinorelbine present in amounts ranging from about 5 mg and about 100 mg, preferably between about 20 mg and about 80 mg per soft capsule. With respect to percentage amounts, the composition of the invention can preferably comprise vinorelbine tartrate in a pharmaceutically effective amount ranging from about 14% to about 18% by weight of the total fill composition weight.

Ethanol is present as a co-solvent with polyethylene glycol in the fill composition of the invention and important to the stability and solubility of vinorelbine and the stability of the capsule shell. The amount and ratio of the ethanol and the polyethylene glycol in the inventive fill composition can be critical to preparing an acceptable soft capsule. During storage of capsules containing compositions with ethanol, the ethanol typically has a tendency to evaporate from the liquid fill composition causing a "dimpling" effect on the capsule. Preferably, the amount of ethanol to be used in the fill composition of the invention is relatively low. Thus, ethanol is present in an amount ranging from about 0.3% to about 7.5% of the total weight of the fill composition. Preferably, ethanol is present in an amount from about 1.6% to about 5% of the total composition weight.

The weight ratio of water to ethanol in the composition of the invention can be from about 2:1 to about 3:1. Preferably, the weight ratio of water to ethanol is from about 2.3:1 to about 2.7:1, more preferably 2.5:1. The water, preferably purified water, content of the composition comprises an amount from about 1% to about 15% of the total weight of the fill composition.

The composition according to the invention can further comprise glycerol, sorbitol and propylene glycol, and mixtures thereof. The total amount of glycerol, sorbitol and/or propylene glycol used in the composition can range from about 0.1% to about 20% of the total weight of the composition, preferably from about 0.2% to about 12%. In an even more preferred embodiment, the total glycerol, sorbitol and/or propylene glycol is present in an amount of between about 0.8% and 1.4% of the total fill weight.

The form of polyethylene glycol which can be used with the invention is the liquid form of polyethylene glycol having an average molecular weight ranging from about 200 to about 600 Daltons. In a preferred embodiment, the polyethylene glycol having an average molecular weight from about 300 to about 400 is used, most preferably 400. Polyethylene glycol can be present in the composition of the invention in an amount ranging from about 66% to about 78% by weight of the total composition.

In a still most preferred embodiment, the soft capsular material comprises a mixture of porcine and bovine gelatin at weight ratios of from 2:1 to 1:2. In the following examples, all percentages are percentages by weight unless expressed otherwise.

EXAMPLES

Soft Capsule Vinorelbine Formulation

Example 1

Vinorelbine Formulation for Soft Capsules

Vinorelbine tartrate is dissolved in the blend of excipients: purified water, ethanol, glycerol and polyethylene glycol 400, using a Becomix mixer or equivalent. An alternative process consist of first dissolving vinorelbine tartrate in purified water and ethanol and secondly adding slowly glycerol and polyethylene glycol 400.

The following soft capsule fill formulation was prepared in accordance with the invention. It is also the best mode of operation for this invention.

| Formula 1 | |
|---|---|
| Ingredient: | Amount: |
| Vinorelbine tartrate | 15.8% |
| Ethanol | 2.9% |
| Purified water | 7.1% |
| Glycerol | 1.1% |
| Polyethylene glycol 400 | 73.1% |
| Total | 100.0% |

The soft capsule shell can be composed of any polymer or polymer mixture which is suitable for use in pharmaceutical soft capsule dosage forms. A variety of such soft capsule materials can be used and are well known to those skilled in the art. See, for example, U.S. Pat. No. 6,340,473. Soft shell capsule materials which can be used include, but are not limited to, those set forth in U.S. Pat. No. 6,340,473. Capsule shell materials can further include plasticizers, such as glycerol, sorbitol and propylene glycol. In a further embodiment, the capsule shell material can further comprise an embrittlement inhibitor. One such inhibitor composition is described in European Patent No. 121,321, the entire text of which is incorporated herein by reference. When an embrittlement inhibitor is used in the shell material, other polyalcohols can be combined with sorbitol and sorbitan mixtures as well. One example of a polyalcohol which can be thusly combined includes hydrogenated polysaccharides. In one embodiment, the capsule material comprises between about 4% and about 25% by weight sorbitol/sorbitan mixture, preferably between about 9% and about 15% by weight, relative to the total weight of the capsule shell.

When gelatin is used as the capsular material, a mixture of porcine and bovine gelatins is preferred. In a still more preferred embodiment, the capsule shell comprises 2 parts of porcine gelatin for every part of bovine gelatin. Other additives, such as coloring agents and lubricants, can be used in the capsule material as well.

The pharmaceutical composition of the invention can be prepared using conventional pharmaceutical composition manufacturing techniques and equipment. Soft capsules which contain the pharmaceutical composition of the invention can also be prepared using conventional soft capsule encapsulation and manufacturing techniques and equipment as well. Encapsulation techniques are well known to those skilled in the art.

Example 2

Comparative Data for Ethanol Content and Ratio Between the Water Content and Ethanol Content Two fill compositions were prepared using different amounts of ethanol in the fill composition. Formula 1 and Formula 2 were prepared following the same process. First vinorelbine tartrate is solubilized in the blend of purified water and ethanol, secondly glycerol and polyethylene glycol 400 are slowly added and mixed until a homogenous mixture was obtained.

The fill compositions evaluated were as follows:

TABLE 1

Vinorelbine Formulations (for a theoretical ratio vinorelbine tartrate/ vinorelbine base equal to 1.385)

|  | Formula 1 | | Formula 2 | |
| --- | --- | --- | --- | --- |
| Ingredient: | (mg) | (%) | (mg) | (%) |
| Vinorelbine tartrate | 55.40 | 15.8 | 55.40 | 26.6 |
| (vinorelbine base) | (40.00) | | (40.00) | |
| ethanol | 10.00 | 2.9 | 20.60 | 9.9 |
| purified water | 25.00 | 7.1 | 12.40 | 6.0 |
| glycerol | 4.00 | 1.1 | 8.80 | 4.2 |
| PEG 400 | 255.60 | 73.1 | 110.80 | 53.3 |
| Total | 350.00 | 100.0 | 208.00 | 100.0 |

The formulations were prepared so that about a 7% by weight difference in the concentration of ethanol in the formulations was present for comparison. Formula 1 had a water to ethanol content ratio of about 2.5:1, whereas the water to ethanol ratio of Formula 2 was about 0.6:1. The fill formulations were then encapsulated in a capsular material composed of a mixture comprising 2 parts porcine and 1 part bovine gelatin.

Dimpling of 100 percent of 20 capsules containing Formula 2 packaged in 50 cc amber glass was observed after 18 months of storage. This "dimpling" phenomenon was due to the evaporation of ethanol from the fill composition. The results demonstrate that both the ethanol content and the water to ethanol ratio present in the fill composition of the invention are important to preserve the desirable properties of both the pharmaceutical composition and the capsule material.

Example 3

Comparative Data of Soft Capsule Vinorelbine Formulations

Five different liquid fill compositions containing vinorelbine were prepared and evaluated for solubility characteristics. Each of the formulations compared were prepared containing the same amount of active vinorelbine tartrate, while varying the presence and amounts of the other ingredients. For each formulation, 50 g to 100 g of fill has been prepared using a laboratory scale disk mixer and by incorporating the drug substance in the different ingredients. Solubility was evaluated by visually checking the clearness of each fill preparation. The composition ingredients and respective amounts are summarized in the following Table 2:

The results from this experiment are summarized in Table 3 as follows:

TABLE 3

Solubility Data

| | Formula 3 | Formula 4 | Formula 5 | Formula 6 | Formula 2 |
| --- | --- | --- | --- | --- | --- |
| Observation | Vinorelbine not totally solubilized | Vinorelbine not totally solubilized | Highly Viscous | Vinorelbine solubilized | Vinorelbine solubilized |

As vinorelbine was not totally solubilized in Formula's 3 and 4, they were not retained for further evaluation. Formula 5 was discarded due to its high viscosity and the impossibility of pumping it to the encapsulation machine. Formula 2 was preferred to Formula 6 because preferably the liquid fill composition should include Polyethylene Glycol 400, in order to preserve a good compatibility with the capsular material. Furthermore, the high percentage of ethanol in Formula 6 could lead to an unacceptable dimpling phenomenon.

The results demonstrate, that water and ethanol need to be present with the polyethylene glycol, as well as present in certain amounts/ratios, in order to provide the desired solubility of vinorelbine in the formulation.

The formulation of the invention increases the concentration of solubilized vinorelbine while at the same time minimizes the presence of both water and ethanol. As can be seen from the data, 20 mg of vinorelbine is not completely solubilized in 10 mg of water, and the attempt to dissolve a 20 mg quantity of vinorelbine in 10 mg of ethanol produces a viscous product. Surprisingly, it has been discovered that 20 mg of vinorelbine can be solubilized in a mixture composed of only 6.20 mg of water and 10.30 mg of ethanol, before the addition of polyethylene glycol, without observable precipitation of vinorelbine. Thus, the formulation of the invention is particularly suitable for soft capsule dosage forms.

Example 4

Vinorelbine Stability Data

The stability of vinorelbine in: 1) powder form (active pharmaceutical ingredient) in a container composed of an aluminum bottle with an internal epoxy varnish, and 2) solubilized in a fill composition for a soft capsule which was packaged in a blister pack, was evaluated by measurement of impurity content and coloration following storage.

TABLE 2

Vinorelbine Formulations (for a theoretical ratio vinorelbine tartrate/vinorelbine base equal to 1.385)

| Ingredient | Formula 3 | % | Formula 4 | % | Formula 5 | % | Formula 6 | % | Formula | % |
| --- | --- | --- | --- | --- | --- | --- | --- | --- | --- | --- |
| Vinorelbine tartrate | 27.70 mg | 73.5 | 27.70 mg | 19.1 | 27.70 mg | 73.5 | 27.70 mg | 62.7 | 27.70 | 26.6 |
| (Vinorelbine base) | (20.00 mg) | | (20.00 mg) | | (20.00 mg) | | (20.00 mg) | | (20.00 mg) | |
| Ethanol | 0 | | 0 | | 10.00 mg | 26.5 | 10.30 mg | 23.3 | 10.30 mg | 9.9 |
| Purified water | 10.00 mg | 26.5 | 11.20 mg | 7.7 | 0 | | 6.20 mg | 14.0 | 6.20 mg | 6.0 |
| Polyethylene glycol 400 | 0 | | 104.60 mg | 72.1 | 0 | | 0 | | 55.40 mg | 53.3 |
| Total Amount | 37.70 mg | 100. | 145.10 mg | 100. | 37.70 mg | 100. | 44.20 mg | 100. | 104.00 | 100 |

Impurity content was measured according to a HPLC method to quantify the presence of active vinorelbine measured at 3, 6, 9, 12, 18 and 24 month intervals. The HPLC chromatographic method used included an assembly fitted with an automatic injector and variable wavelength UV detector set at 267 nm. The column was stainless steel with a length of 150 mm and diameter of 3.9 mm and filled with octadecylsilyl silica gel—300 Å—spherical, 5 µm. The mobile phase was carried out with sodium decanesulfonate (1.2217 g), phosphate buffer 0.05 M (pH=4.2) 380 ml, and methanol (620 ml), with a thermostatically-controlled column temperature of +40° C. and a mobile phase flow rate of 1 ml/min.

Each batch was stored over the analysis time at 5° C.±3° C.

Mean variation was calculated as from the difference between the average of the results at the per given analysis time and the average of the results at the initial time ($t_0$) for several batches (3 batches for the vinorelbine powder, 3 batches for the 20 mg soft capsules, 4 batches for the 30 mg soft capsules, 3 batches for the 40 mg soft capsules, 3 batches for the 80 mg soft capsules.)

The results are summarized in the following table:

TABLE 5

Relative Area Percent Impurity Content

| | Analysis time (months) | | | | | |
|---|---|---|---|---|---|---|
| | 3 | 6 | 9 | 12 | 18 | 24 |
| Vinorelbine (powder): | | | | | | |
| Mean variation ($t_0 \rightarrow$ analysis time) | n.p. | 0.12 | n.p. | 0.39 | 0.78 | 1.13 |
| Max. variation ($t_0 \rightarrow$ analysis time) | n.p. | 0.21 | n.p. | 0.44 | 0.85 | 1.32 |
| Vinorelbine (liquid): | | | | | | |
| Mean variation ($t_0 \rightarrow$ analysis time) | 0.08 | 0.15 | 0.12 | 0.15 | 0.16 | 0.10 |
| Max. variation ($t_0 \rightarrow$ analysis time) | 0.25 | 0.36 | 0.32 | 0.42 | 0.42 | 0.32 | n.p. = not performed

As can be seen from the results, the liquid fill composition containing solubilized vinorelbine in a soft capsule exhibited a much lower percentage value of impurities at 12, 18 and 24 month time periods. The results demonstrate that the liquid vinorelbine formulation of the invention possesses increased longevity in storage as compared to the powder form of the drug.

Example 5

Comparative Color Evolution

The comparative evolution color was also evaluated for each sample and corresponding time interval as set forth in Example 4. In this experiment, pure powder form vinorelbine was compared to soft capsule encapsulated vinorelbine liquid fill composition of the invention (Formula 1.). Coloration was measured at 5° C.±3° C. by ultraviolet absorbance at 420 nm of aqueous vinorelbine at 10 mg/ml expressed as vinorelbine base. The coloration data is indicative of vinorelbine degradation as non-chromatographied oxidative impurities. Mean variation was calculated as from the difference between the average of the results at the per given analysis time and the average of the results at the initial time ($t_0$) for several batches (3 batches for the vinorelbine powder, 3 batches for the 20 mg soft capsules, 4 batches for the 30 mg soft capsules, 3 batches for the 40 mg soft capsules, 3 batches for the 80 mg soft capsules.)

The results are summarized in the following table:

TABLE 6

Color Evolution Data

| | Analysis time (months) | | | | | |
|---|---|---|---|---|---|---|
| | 3 | 6 | 9 | 12 | 18 | 24 |
| Vinorelbine (powder): | | | | | | |
| Mean variation ($t_0 \rightarrow$ analysis time) | n.p. | 0.006 | n.p. | 0.013 | 0.017 | 0.029 |
| Max. variation ($t_0 \rightarrow$ analysis time) | n.p. | 0.012 | n.p. | 0.015 | 0.025 | 0.041 |
| Vinorelbine (liquid): | | | | | | |
| Mean variation ($t_0 \rightarrow$ analysis time) | 0.000 | 0.002 | 0.005 | 0.005 | 0.005 | 0.006 |
| Max. variation ($t_0 \rightarrow$ analysis time) | 0.015 | 0.006 | 0.011 | 0.006 | 0.021 | 0.017 | n.p. = not performed

As can be seen from the above data, the liquid vinorelbine composition exhibits higher purity over time at the 6, 12, 18 and 24 month analysis times as compared to the powdered form of the drug when using coloration as an indicator of storage stability.

Example 6

Comparative Data for Capsular Material

Multiple samples of two capsule types containing identical fill compositions were prepared and tested for capsule fragility.

The composition of the two different capsules is set forth as follows:

TABLE 7

Soft Capsule Composition

| | Capsule 1 | Capsule 2 |
|---|---|---|
| Fill ingredients: | | |
| Vinorelbine tartrate | 55.40 mg | 55.40 mg |
| (vinorelbine base) | (40.00 mg) | (40.00 mg) |
| ethanol | 10.00 mg | 10.00 mg |
| purified water | 25.00 mg | 25.00 mg |
| glycerol | 4.00 mg | 4.00 mg |
| polyethylene glycol 400 | 255.60 mg | 255.60 mg |
| Capsule gelatin type: | | |
| Porcine | 2 parts | none |
| Bovine | 1 part | all |

The soft capsules were stored for a period of two (2) years at a temperature of 5° C.±3° C. Ten capsules of each were subjected to crushing tests performed using a dynamometric plier, and the mean force values calculated from each test. The mean force for Capsule 1 was 160 N, whereas the mean force for Capsule 2 was 98 N. Capsule 2, therefore, exhibited greater fragility as compared to Capsule 1.

As can be seen from the above data, capsular material composition itself can affect the structural integrity of the dosage form even when identical fill compositions are encapsulated within. Capsule 1 containing the mixture of porcine and bovine gelatins as the gelatin source exhibited increased resistance to crushing forces as compared to Capsule 2 containing bovine gelatin alone as the gelatin source.

Method of Treatment Using Soft Capsules Containing Vinorelbine

Oral administration of soft capsules comprising vinorelbine prepared in accordance with the invention can be used to treat cancers responsive to vinorelbine by inhibiting cancer cell growth. The anti-neoplastic and anti-mitotic effects of vinorelbine by way of inhibiting tubulin polymerization are realized in association with the systemic bioavailability of the drug substance by the oral administration route afforded by the invention.

INDUSTRIAL APPLICABILITY

The invention can be used in chemotherapy for cancer patients in which the administration of vinorelbine and its associated anti-neoplastic and anti-mitotic effects can be beneficial. The invention is especially useful in situations wherein oral administration is desirable or preferable to the intravenous administration route.

Each patent and publication cited in this application is incorporated by reference as if the full text of each were individually incorporated by reference. The invention has been described herein above with reference to various specific and preferred embodiments and techniques. It will be understood, however, that reasonable modifications and variations of such embodiments and techniques can be made without significantly departing from either the spirit or scope of the invention as defined by the claims below.

What we claim is:

1. A liquid oral pharmaceutical composition suitable as a liquid fill composition for a soft capsule dosage form, said composition comprising:
   a) vinorelbine or a pharmaceutically acceptable salt thereof;
   b) ethanol present in an amount ranging from about 0.3% to about 7.5% by weight of the total weight of the fill composition;
   c) water;
   d) glycerol; and
   e) polyethylene glycol;
   wherein the weight ratio of water to ethanol in the composition ranges from about 2:1 to about 3:1.

2. The pharmaceutical composition according to claim 1, wherein said soft capsule dosage form is a soft gelatin capsule.

3. The pharmaceutical composition according to claim 2 wherein said gelatin is a mixture of porcine and bovine gelatin.

4. The pharmaceutical composition according to claim 1, wherein said pharmaceutically acceptable salt of vinorelbine is vinorelbine tartrate.

5. The pharmaceutical composition according to claim 1, wherein said polyethylene glycol has an average molecular weight ranging from about 200 to about 600.

6. The pharmaceutical composition according to claim 5 wherein the polyethylene glycol is polyethylene glycol 400.

7. The pharmaceutical composition according to claim 1, wherein said composition comprises:
   a) vinorelbine tartrate present in an amount ranging from about 5 mg to about 100 mg per capsule;
   b) ethanol present in an amount ranging from about 0.3% by weight to about 7.5% by weight of the total weight of the fill composition;
   c) water present in an amount ranging from about 1% by weight to about 15% by weight of the total weight of the fill composition;
   d) glycerol present in an amount ranging from about 0.1% by weight to about 20% by weight of the total weight of the fill composition;
   e) polyethylene glycol 400 present in an amount ranging from about 66% by weight to about 78% by weight of the total weight of the fill composition.

8. The pharmaceutical composition according to claim 7, wherein said composition comprises:
   a) vinorelbine tartrate present in an amount ranging from about 5 mg to about 100 mg per capsule;
   b) ethanol present in an amount ranging from about 1.6% by weight to about 5% by weight of the total weight of the fill composition;
   c) water present in an amount ranging from about 1% by weight to about 15% by weight of the total fill composition;
   d) glycerol present in an amount ranging from about 0.2% by weight to about 12% by weight of the total weight of the fill composition;
   e) polyethylene glycol 400 present in an amount ranging from about 66% by weight to about 78% by weight of the total weight of the fill composition.

9. The pharmaceutical composition according to claim 1 wherein the weight ratio of water to ethanol in the composition ranges from about 2.3:1 to about 2.7:1.

10. The pharmaceutical composition according to claim 1 wherein the weight ration of water to ethanol in the composition is about 2.5:1.

11. A method of treating cancer comprising orally administering, to a patient in need of treatment thereof, a pharmaceutical composition comprising:
   a) a pharmaceutically effective amount of vinorelbine or a pharmaceutically acceptable salt thereof;
   b) ethanol present in an amount ranging from about 0.3% to about 7.5% by weight of the total weight of the fill composition;
   c) water;
   d) glycerol; and
   e) polyethylene glycol present in an amount ranging from about ranging from about 66% by weight to about 78% by weight of the total weight of the fill composition;
   wherein said composition is encapsulated within a soft capsule; and
   wherein the weight ratio of water to ethanol in the composition ranges from about 2:1 to about 3:1.

12. The pharmaceutical composition according to claim 8 wherein said composition comprises:
   a) about 15.8% by weight of vinorelbine tartrate;
   b) about 2.9% by weight ethanol;
   c) about 7.1% by weight water;
   d) about 1.1% by weight glycerol; and
   e) about 73.1% by weight polyethylene glycol 400.

* * * * *